United States Patent

Nagakura et al.

[11] 3,962,340
[45] June 8, 1976

[54] 1,2,6-TRIMETHYLTRICYCLO-[5,3,2,0$^{2,7}$]DODECA-5-ONE

[75] Inventors: Akira Nagakura, Kawaguchi; Susumu Akutagawa, Yokohama; Haruki Kurihara, Tokyo, all of Japan

[73] Assignee: Takasago Perfumery Co., Ltd., Tokyo, Japan

[22] Filed: Dec. 27, 1974

[21] Appl. No.: 537,005

[30] Foreign Application Priority Data
Jan. 11, 1974  Japan.................. 49-6389

[52] U.S. Cl............................ 260/586 G; 252/522; 260/348 C; 260/348.5 L; 260/586 R; 260/666 PY
[51] Int. Cl.$^2$......................................... C07C 49/36
[58] Field of Search ......... 260/586 G, 586 P, 586 R

[56] References Cited
UNITED STATES PATENTS

| | | | |
|---|---|---|---|
| 2,393,607 | 1/1946 | Bruson............................ | 260/586 G |
| 2,942,029 | 6/1960 | Buchi et al....................... | 260/586 G |
| 2,968,660 | 1/1961 | Buchi et al. ..................... | 260/586 P |
| 3,052,729 | 9/1962 | Eschinazi......................... | 260/586 P |
| 3,446,755 | 5/1969 | Saunders......................... | 260/586 G |
| 3,678,119 | 7/1972 | Kitchens et al. ................. | 260/586 G |
| 3,711,553 | 1/1973 | Schmid et al................... | 260/586 G |
| 3,729,513 | 4/1973 | Berezin........................... | 260/586 G |
| 3,835,192 | 9/1974 | Van Der Linde et al........ | 260/586 G |
| 3,836,584 | 9/1974 | Frater et al..................... | 260/586 G |

*Primary Examiner*—Norman Morgenstern
*Attorney, Agent, or Firm*—Sughrue, Rothwell, Mion, Zinn & Macpeak

[57] ABSTRACT

1,2,6-Trimethyltricyclo[5,3,2,0$^{2,7}$]dodeca-5-one having the formula (I)

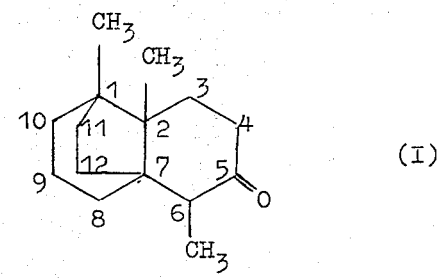

and a process for producing this compound. This compound is useful as a perfume.

1 Claim, 4 Drawing Figures

Re: 49-6389

Re: 49-6389

1,2,6-TRIMETHYLTRICYCLO[5,3,2,0$^{2,7}$]DODECA-5-ONE

BACKGROUND OF THE INVENTION

1. Field of the Invention

This invention relates to a tricyclic hydrocarbon, 1,2,6-trimethyltricyclo[5,3,2,0$^{2,7}$]dodeca-5-one, and to a process for producing this tricyclic hydrocarbon compound.

2. Description of the Prior Art

Amber-like fragrant substances are important starting materials for a blended perfume, and of these substances, ambergris obtainable from sperm whales is the most expensive. The fragrance component of ambergris was clarified by E. Iaderer and L. Ruzicka in 1946 to be a substance formed from ambrein which is a triterpene compound. Ever since, many attempts to synthesize amber-like fragrant substances equal to the natural material, or similar substances have been made. Some of them can be utilized as a substitute for expensive ambergris. For example, manool derivatives, which are diterepene compounds and can be obtained from a special needle-leaf tree, are widely used as such a substitute. However, in general, amber-like fragrant substances are difficult to synthesize and moreover, special natural products are required as a starting material to synthesize amber-like fragrant substances. Therefore, synthetic amber-like fragrant substances are inevitably expensive.

SUMMARY OF THE INVENTION

This invention provides 1,2,6-trimethyltricyclo[5,3,2,0$^{2,7}$]dodeca-5-one having the formula

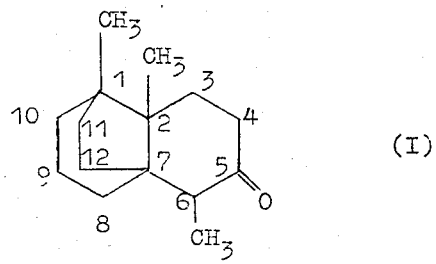

and a process for producing 1,2,6-trimethyltricyclo[5,3,2,0$^{2,7}$]dodeca-5-one (hereinafter "Compound (I)") comprising isomerizing 5,6epoxy-1,2,6-trimethyltricyclo[5,3,2,0$^{2,7}$]dodecane (herein after referred to as "Compound (II)") with a Lewis acid.

BRIEF DESCRIPTION OF THE ACCOMPANYING DRAWINGS

DETAILED DESCRIPTION OF THE INVENTION

Figure 1:
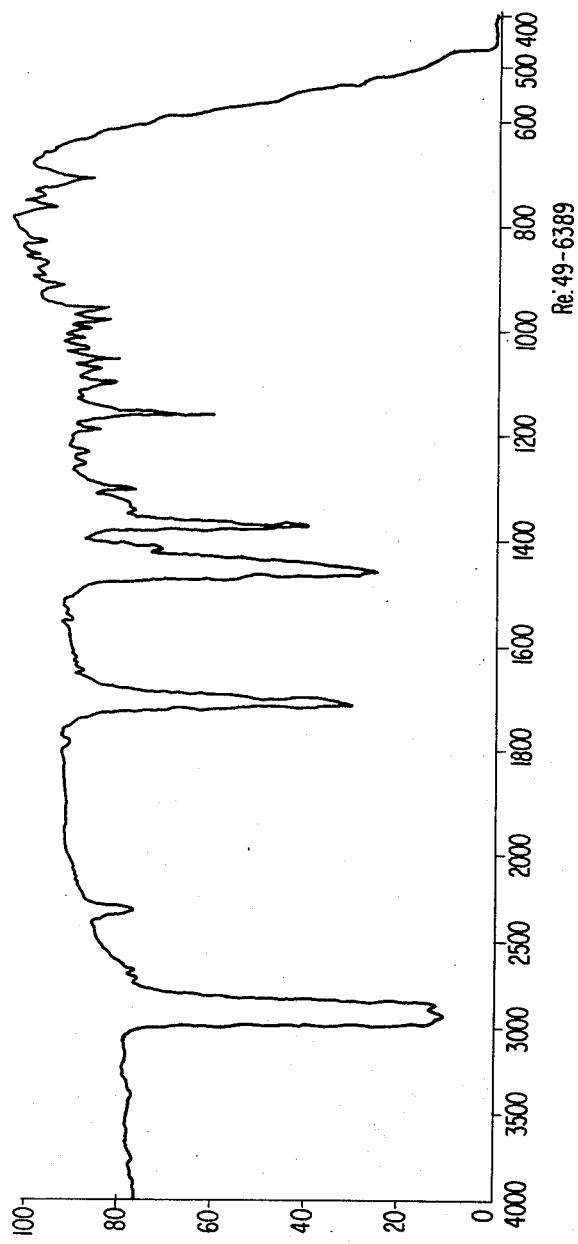
FIG. 1 is an infrared spectrum of Compound (I) obtained according to the present invention.
Figure 2:
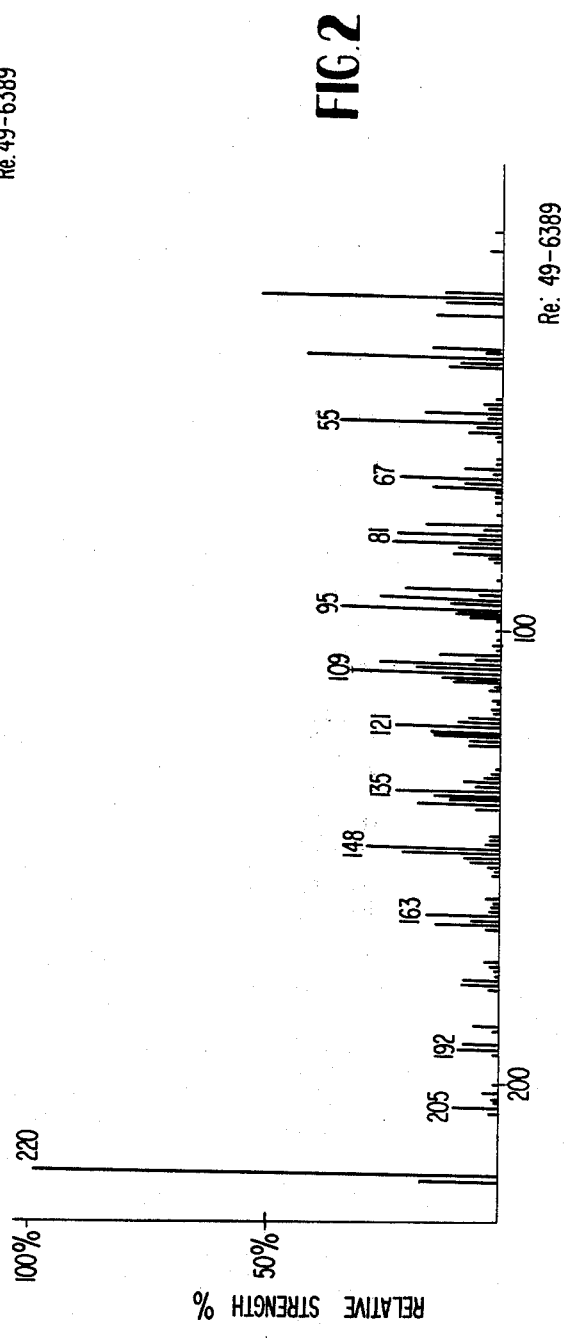
FIG. 2 is a mass spectrum of Compound (I) obtained according to the present invention.
Figure 3:
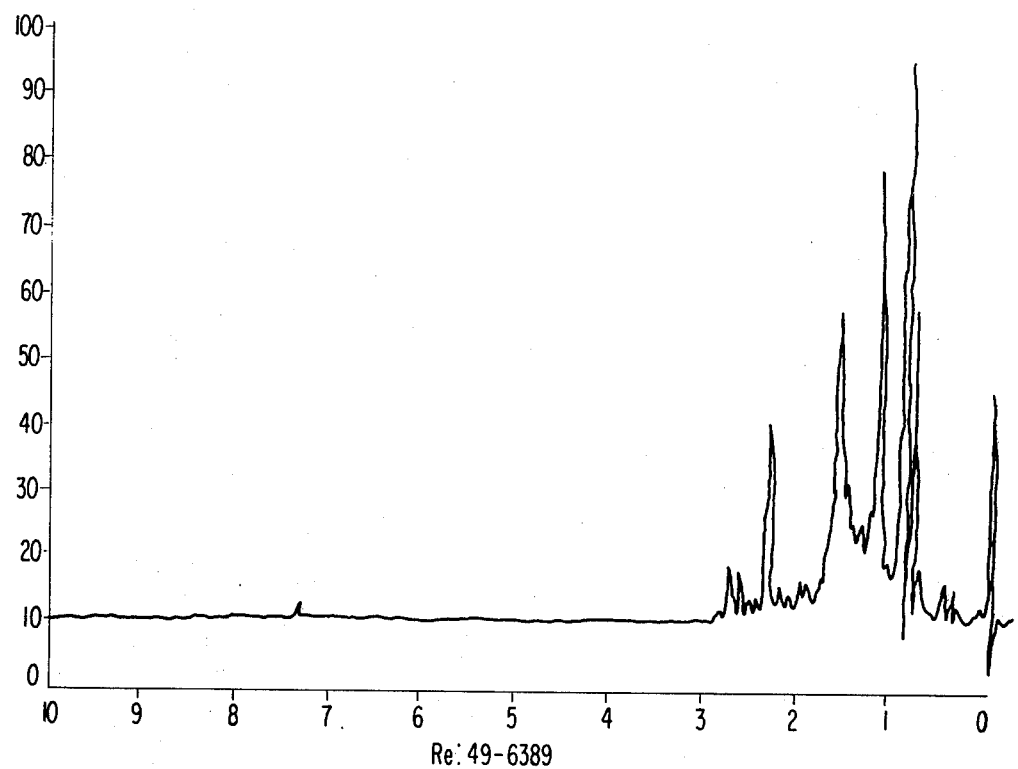
FIG. 3 is an NMR spectrum of Compound (I) obtained according to the present invention.

Compound (I) produced according to the present invention is a sesquiterpene compound having the molecular formula, $C_{15}H_{24}O$, and a structure represented by the formula (I)

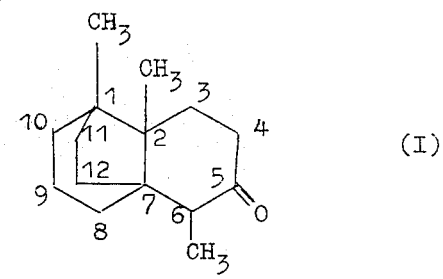

According to this invention, Compound (I) can be obtained much more cheaply than conventional amber-like fragrant substances, and is also of industrial value because of its excellent amber-like fragrance.

According to the present invention, Compound (I) can be prepared by adding Compound (II) dropwise to a mixed solution of a Lewis acid such as AlX$_3$, ZnX$_2$ and MgX$_2$ (wherein X is Cl, Br or I) or a boron trifluoride-diethyl ether complex salt, etc. and a solvent inert to the Lewis acid, e.g., ethers such as diethyl ether, dipropyl ether, etc., hydrocarbons such as n-hexane, n-octane, benzene, toluene, etc., halogenated hydrocarbons such as dichloromethane, chloroform, etc., esters such as ethyl acetate, butyl acetate, etc., and the like, at a temperature of about −10° to 30°C, and isomerizing Compound (II) with the Lewis acid. Alternatively the reaction can be conducted in the absence of an inert solvent but the reaction proceeds more smoothly when an inert solvent is employed.

When the boron trifluoride-diethyl ether complex salt is used as a Lewis acid, a suitable amount thereof is about one-twentieth to one-thirtieth mole per mole of Compound (II). Further, when other Lewis acids are used, a suitable amount thereof is about 0.1 to 1.2 moles per mole of Compound (II), with 1 mole being preferred to achieve an isomerization which proceeds most smoothly and in which better results are obtained. A preferred isomerization temperature is 5° to 10°C. When the isomerization temperature exceeds about 30°C, a large amount of polymeric materials are formed. The isomerization is sensitive to moisture and, thus anhydrous conditions are employed and the isomerization is preferably carried out in a dry air or a dry nitrogen atmosphere. A sufficient isomerization time in the preferred isomerization temperature range as described above is about 4 to 5 hours. After completion of the isomerization, the resulting solution is acidified, i.e., with cold dilute hydrochloric acid, dilute sulfuric acid, etc., and then extracted with a solvent such as diethyl ether, benzene, etc. Subsequently, the extract is distilled in vacuo, whereby crystalline Compound (I) can be obtained in a yield of 75% or more.

Compound (II) used as a starting material in the process of this invention can be produced by subjecting 1,5,9-trimethylcyclododecatriene-1,5,9 (hereinafter 1,5,9-TMCDT), which is a cyclic trimer of isoprene to an intramolecular ring closure reaction with an acid catalyst to form 1,2,6-trimethyltricyclo[5,3,2,0$^{2,7}$]dodeca-5-ene (hereinafter "Compound (III)"), and treating this compound with a peracid. The intramolecular ring closure reaction and the reaction with the peracid are, respectively, disclosed in copending U.S. Patent Applications Ser. No. 537,004, filed Dec. 27, 1974, (corresponding to Japanese Patent Application Nos. 4207/1974 and 102646/74) and Ser. No. 537,039, filed Dec. 27, 1974, (corresponding to Japanese Patent Application No. 6388/1974) both filed simultaneously herewith.

Compound (I) is a fragrant substance having a rich natural ambergris-like fragrance, a peculiar wood-like odor, a camphor-like diffusibility and a so called "natural odor" reminiscent of moist earth or a sunshiney forest. When Compound (I) is absorbed on filter paper, and allowed to stand in a room at room temperature, (e.g., about 20°–30°C) the residual fragrance is very strong and lasts for over 1 week. The fragrant odor of Compound (I) also is strong and even when Compound (I) is diluted with ethyl alcohol, the average person even can perceive Compound (I) even at a one-tent-housandth dilution.

The utility value and application range of Compound (I) of this invention are wide as a perfumery material. That is, Compound (I) can be widely used as a perfume, for example, as a component for a rich perfume to a perfume for a relatively inexpensive soap, by utilizing its residual fragrance and economy. It is possible to use Compound (I) together with rich natural amber, or musk civet, or as a substitute therefor by utilizing its ambergris-like fragrance, or together with natural sandalwood oil, vetiver oil, patchouli oil, cedar oil, etc., or as a substitute therefor by utilizing its wood-like fragrance, thereby providing a dry and rough scent necessary for a man's perfume.

Now, the present invention will be described in detail, by reference to the following Reference Example, Examples and drawings. The examples are merely illustrative and are not to be construed as limiting the scope of the present invention. Unless otherwise indicated, all parts, percents, ratios and the like are by weight.

REFERENCE EXAMPLE i. Process for Preparing 1,2,6-trimethyltricyclo[5,3,2,0$^{2,7}$]dodeca-5-ene, Compound (III), from 1,5,9-trimethylcyclododecatriene-1,5,9, 1,5,9-TMCDT Into a 1l three-necked flask were charged 150 g of 1,5,9-trimethylcyclododecatriene-1,5,9 (melting point: 91°–92°C), 260 ml of formic acid and 150 ml of dichloromethane, and the materials were mixed. The mixture was kept at a temperature of 5° to 10°C. Then, a mixture of 7.5 ml of sulfuric acid and 40 ml of formic acid was added dropwise thereto over a period of 30 minutes, while keeping the temperature at 5° to 10°C. Subsequently, the materials were reacted with stirring at that temperature for 3 hours, and further reacted with stirring at room temperature (i.e., about 20°–30°C) for 3 additional hours. After completion of the reaction, dichloromethane was recovered by distillation, and formic acid was then distilled off under reduced pressure. The residue was neutralized and washed with a 3% aqueous sodium bicarbonate solution, washed with water, and dried with anhydrous sodium sulfate. Then, the residue was distilled in vacuum, whereby 135 g of the fraction of 1,2,6-trimethyltricyclo[5,3,2,0$^{2,7}$]dodeca-5-ene (75°–80°C/0.05 mmHg) was obtained.

ii. Process for Preparing Compound (II) from 1,2,6-trimethyltricyclo[5,3,2,0$^{2,7}$]dodeca-5-ene, Compound (III)

A mixture of 20.4 g (0.1 mole) of 1,2,6-trimethyltricyclo[5,3,2,0$^{2,7}$]dodeca-5-ene and 17 g of sodium carbonate was added to 100 ml of dichloromethane, and the materials were mixed and stirred while keeping the temperature at 0° to 5°C. Then, 20.8 g (0.11 mole) of an acetic acid solution containing 40% peracetic acid was added dropwise thereto over a period of 2 hours at that temperature. The materials were stirred at that temperature for 2 hours, and further stirred at room temperature for 3 additional hours. Subsequently, 200 ml of water was added thereto, and the resulting solution was extracted twice with dichloromethane. The extract was washed with an aqueous saturated sodium chloride solution until the solution became neutral, and then dried with anhydrous sodium sulfate. Dichloromethane was then recovered by distillation, and the residue was distilled in vacuum, whereby 21 g of the fraction of Compound (II) (85°–90°C/0.03 mmHg) was obtained.

EXAMPLE 1

13.4 g (0.1 mole) of AlCl$_3$ and 100 ml of n-hexane were mixed under a dry nitrogen atmosphere, and the mixture was kept at 0° to 10°C. 22 g (0.1 mole) of Compound (II) was added dropwise thereto over a period of one hour. The materials were stirred at that temperature for one hour, and further stirred at room temperature for 2 additional hours. Then, the reaction solution was poured into 100 ml of cold dilute hydrochloric acid (6N), and the solution was extracted with n-hexane. The extract was dried with anhydrous sodium sulfate, and n-hexane was then distilled off. Subsequently, the residue was distilled in vacuum, whereby 20 g of the fraction (105°–110°C/0.05 mmHg) corresponding to Compound (I) was obtained. By recrystallizing this compound from methanol, 17.6 g of prism-like crystalline Compound (I) having a melting point of 99.5° to 100.5°C was obtained in a yield of 80%.

| Elemental Analysis: | C | H |
| --- | --- | --- |
| Calculated (%): | 81.76 | 10.98 |
| Found (%) : | 81.75 | 10.98 |
| IR Spectrum: | 1710 cm$^{-1}$ | ($\gamma$C=O) |
| MAS Spectrum: | M$^+$ | 220 (molecular ion) |
|  | M$^+$—CH$_3$ | 205 |
|  | M$^+$—CO | 192 |

NMR Spectrum:

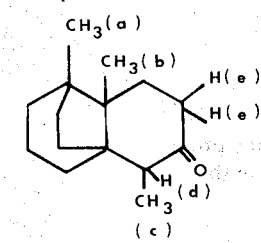

(a) 0.95 ppm (3H, s)
(b) 1.20 ppm (3H, s)
(c) 0.89 ppm (3H,d,J=7cps)
(d) 2.77 ppm (1H,q,J=7cps)
(e) 2.37 ppm (2H,m)

X-ray Crystal Structural Analysis (direct method):
Lattice constant: $a=7.975$A, $b=13.225$A, $c=7.147$A, $\alpha=95.7°$, $\beta=60.0°$, $\gamma=104.2°$
Space group: $P\bar{1}$, $Z=2$
Values (A) of X, Y and Z as solid coordinates:

| Atom | RX | RY | RZ |
|---|---|---|---|
| C1 | 0.9791 | 5.7703 | 1.7584 |
| C2 | 2.3424 | 5.6967 | 2.4672 |
| C3 | 3.1955 | 4.4961 | 2.0121 |
| C4 | 2.3586 | 3.2151 | 1.9691 |
| C5 | 3.0098 | 1.9672 | 1.2955 |
| C6 | 3.6074 | 2.3334 | −0.0927 |
| C7 | 2.4712 | 2.8519 | −1.0345 |
| C8 | 1.5720 | 3.8637 | −0.3559 |
| C9 | 1.1293 | 3.4170 | 1.0436 |
| C10 | 0.2013 | 4.4893 | 1.6283 |
| C11 | 0.5477 | 1.9829 | 0.9738 |
| C12 | 1.7833 | 1.0214 | 1.1082 |
| C13 | −1.1340 | 4.7008 | 0.8295 |
| C14 | 1.9438 | 2.8689 | 3.4240 |
| C15 | 4.1078 | 1.2928 | 2.1657 |
| O1 | 0.5492 | 6.8548 | 1.4110 |

Bonding angle among atoms from the solid coordinates:

| Three Atoms | Bonding Angle (degree) |
|---|---|
| C2-C1-C10 | 117.21 |
| C1-C2-C3 | 113.06 |
| C3-C4-C9 | 109.94 |
| C5-C4-C14 | 109.74 |
| C4-C5-C12 | 102.04 |
| C6-C5-C15 | 109.29 |
| C6-C7-C8 | 112.52 |
| C4-C9-C10 | 110.05 |
| C8-C9-C11 | 109.68 |
| C1-C10-C13 | 111.65 |
| C5-C12-C11 | 104.92 |
| C2-C1-O1 | 119.15 |
| C2-C3-C4 | 110.94 |
| C3-C4-C14 | 107.85 |
| C9-C4-C14 | 112.11 |
| C4-C5-C15 | 113.57 |
| C12-C5-C15 | 111.06 |
| C7-C8-C9 | 112.68 |
| C4-C9-C11 | 101.76 |
| C10-C9-C11 | 115.93 |
| C9-C10-C13 | 114.50 |
| C10-C1-O1 | 123.46 |
| C3-C4-C5 | 116.95 |
| C5-C4-C9 | 100.20 |
| C4-C5-C6 | 110.94 |
| C6-C5-C12 | 109.74 |
| C5-C6-C7 | 109.65 |
| C4-C9-C8 | 110.69 |
| C8-C9-C10 | 108.58 |
| C1-C10-C9 | 108.39 |
| C9-C11-C12 | 105.50 |

Figure 4:
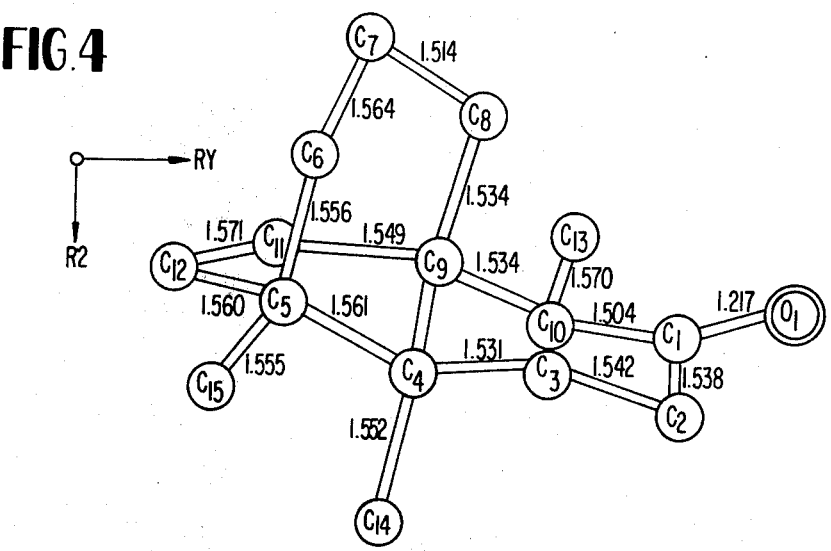
FIG. 4 shows the stereostructural form of a ketone compound obtained by isomerization of Compound (I).

The stereostructural formula shown in FIG. 4 can be derived from the foregoing values.

Molecular Formula: $C_{15}H_{24}O$

From the foregoing results, Compound (I) was determined to have the following stereostructural formula (III)

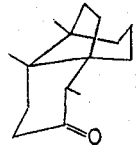

(III)

EXAMPLE 2

The reaction was carried out under the same conditions as described in Example 1, except that 0.57 g (0.004 moles) of boron trifluoride-diethyl ether complex salt was used in place of 13.4 g (0.1 mole) of AlCl$_3$, whereby 17.2 g of Compound (I) was obtained in a yield of 78%.

EXAMPLE 3

The following formulation is suitable as a base for a perfume or an eau-de-cologne.

| | g |
|---|---|
| Civet Absolute | 10 |
| Musk Absolute | 5 |
| Oak Moth Absolute | 30 |
| Vanilla Absolute | 10 |
| Musk Ambrette | 80 |
| Sandalwood Oil | 50 |
| Patchouli Oil | 80 |
| Methyl Ionone | 30 |
| Vetiver Oil | 100 |
| Eugenol | 20 |
| Phenylethyl Alcohol | 30 |
| Geraniol | 30 |
| Benzyl Acetate | 30 |
| Jasmine Absolute | 20 |
| Hexylcinnamic Aldehyde | 50 |
| Linalool | 50 |
| Linalyl Acetate | 50 |
| Bergamot Oil | 125 |
| Compound (I) | 50 |
| | 850g |

EXAMPLE 4

The following formulation is suitable for a soap perfumery.

| | g |
|---|---|
| Ethylene Brassylate | 90 |
| Sandalwood Oil | 50 |
| Oakmoth Resinoid | 10 |
| Patchouli Oil | 50 |
| Coumarin | 30 |
| Bornyl Acetate | 15 |
| Citronellol | 60 |
| Tetrahydrogeraniol | 5 |
| Petigrain Oil | 30 |
| Lavandine Oil | 80 |
| Stearyl Acetate | 15 |
| Pineneedle Oil | 10 |
| Linalool | 185 |
| Linalyl Acetate | 120 |
| Compound (I) | 50 |
| | 800 g |

While the invention has been described in detail and with reference to specific embodiments thereof, it will be apparent to one skilled in the art that various changes and modifications can be made therein without departing from the spirit and scope thereof.

What is claimed is:
1. 1,2,6-Trimethyltricyclo[5,3,2,0$^{2,7}$]dodeca-5-one having the formula (I)

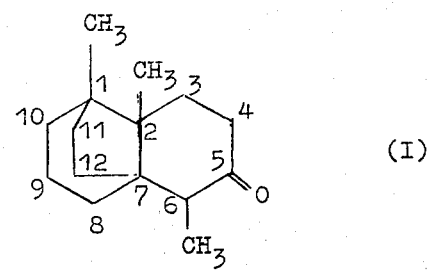

(I)

* * * * *